United States Patent [19]

de Hey et al.

[11] Patent Number: 4,996,069

[45] Date of Patent: Feb. 26, 1991

[54] PROCESS FOR THE PREPARATION OF FLAVOR AND FRAGRANCE MATERIALS

[75] Inventors: Johannes T. de Hey, Hilversum; Harrie Renes, Blaricum; Jan Visser, Huizen, all of Netherlands

[73] Assignee: Unilever Patent Holdings B.V., Rotterdam, Netherlands

[21] Appl. No.: 436,801

[22] Filed: Nov. 15, 1989

[30] Foreign Application Priority Data

Nov. 18, 1988 [NL] Netherlands ........................ 8802848

[51] Int. Cl.$^5$ ................................................ A23L 1/00
[52] U.S. Cl. ................................. 426/248; 204/157.88; 426/650
[58] Field of Search ..................... 426/248, 650; 512/5; 204/157.88

[56] References Cited

U.S. PATENT DOCUMENTS 2,959,521 11/1960 Zajic ....................................... 435/67
4,351,346 9/1982 Brummer et al. .................... 426/248

FOREIGN PATENT DOCUMENTS 0035683 9/1981 European Pat. Off. .
7105166 3/1972 Netherlands .
1130230 10/1968 United Kingdom .

OTHER PUBLICATIONS

S. Isoe et al, "Photo-Oxygenation of Carotenoids . . .", Tetrahedron Letters, No. 4, 1969, Pergamon Press (GB).
Fenaroli's Handbook of Flavor Ingredients, 1971, Chemical Rubber Co., "-Ionone".
S. Arctander: Perfume and Flavor Chemicals (Aroma Chemicals), I, 1969.
Hohler et al., Chem. Mikrobiol. Technol. Lebensm., 11:115–126 (1988).

Primary Examiner—George Yeung
Attorney, Agent, or Firm—Cushman, Darby & Cushman

[57] ABSTRACT

The invention relates to a process for the preparation of flavor and fragrance materials by oxidizing a solution of carotene in an aprotic solvent under the influence of ultra-violet light. The carotene may be synthetic or obtained by extraction with an aprotic solvent or solvent mixture of carotene-containing vegetable material or micro-organisms, which are suitable for human consumption. The reaction is preferably carried out at ambient temperature with UV light with a wave length of 350–560 nm.

11 Claims, No Drawings

PROCESS FOR THE PREPARATION OF FLAVOR AND FRAGRANCE MATERIALS

The invention relates to a process for the preparation of flavour and fragrance materials based on, inter alia. extracts of vegetable material.

From European patent application 035.683 a process is known for the preparation of flavour materials intended for tobacco, whereby, from green tobacco plants or parts thereof, an alcoholic extract containing carotenoids is prepared that is free of chlorophyll and also of waxy diterpene components present on the surface of the tobacco plants, whereafter this alcoholic extract is oxidized under the influence of ultraviolet light. With this process, possibly other alcoholic, xanthophyll-containing plant extracts can be used. However, any illustration of this possibility is missing in this European patent application.

As appears from the above, according to European patent application 035.683 only alcoholic solutions of carotenoids, such as in methanol or ethanol, are used, which means that in these solutions practically no carotenes are present. Further it has proved that the nature and/or the applicability of the flavour materials obtained leaves something to be desired since these flavour materials normally have to be fractionated before use in order to remove undesirable components.

Surprisingly, it has now been found that carotene-containing solutions prepared with the aid of an aprotic solvent, such as extracts of, inter alia, vegetable materials, are exceptionally suitable as starting material for the preparation of flavour and fragrance materials, which solutions, after a photochemical conversion with oxygen, lead to products containing flavour and/or fragrance materials which, after the removal of the aprotic solvent, can be used without any further processing, such as fractionation, for all kinds of purposes, such as flavouring of foodstuffs and stimulants and composing of perfumes.

More particularly, the invention relates to a process for the preparation of flavour and fragrance materials wherein, a solution of carotene in an aprotic solvent is oxidized with oxygen under the influence of ultraviolet light and subsequently the aprotic solvent is substantially removed from the reaction product. The carotene may be obtained from carotene-containing vegetable materials or micro-organisms by extraction with the aid of an aprotic solvent, or the carotene may be of synthetic origin.

From Tetrahedron Letters, N° 4, 1969, pages 279–281, the formation of, inter alia, dihydroactinidiolide and $\beta$-ionone is known, whereby the $\beta$-carotene as solution in benzene and methanol is oxidized under the influence of ultraviolet light in the presence or absence of a sensitizer such as a catalytic amount of alkali and "Bengal rosa". However, from this citation it can by no means be deduced whether the product obtained in this manner could be used as flavour or fragrance material.

As starting material for the process according to the invention can be used, as mentioned, carotenes obtained by extraction with an aprotic solvent of carotene-containing vegetable materials, especially those which are acceptable for human consumption. Examples of such materials are, in particular, edible parts of plants, such as carrots, green tea, paprikas and tomatoes. Other less obvious examples are leaves of all edible green plants, such as even grape vine leaves, which in principle are considered acceptable for human consumption.

Besides the vegetable materials, carotene-containing micro-organisms and algae can likewise be extracted, especially micro-organisms that grow on fruits. More particularly, reference is made to U.S. patent specification 2,959,521, in which the microbial production of $\beta$-carotene with *Choaneohora trispora* is described.

Within the framework of the invention, the term "carotene" means both natural and synthetic carotene products. Further information about the carotene products of natural origin is given in Straub, O. "Lists of Natural Carotenoids" in Carotenoids, 1971, pages 771–850, particularly pages 771–779. More particularly to be understood by the term "carotene" are $\alpha$-carotene, $\beta$-carotene, mixtures of $\alpha$- and $\beta$-carotene with gamma-carotene, lycopene and 15,15'-dihydro-$\beta$-carotene. Advantageously used in the process according to the invention is a commercially available synthetic $\beta$-carotene product.

The mixture of compounds formed by the process according to the invention has a fruity and fresh character that, according to the starting material, can be supplemented with a variety of other notes such as hay-like, yellow, tobacco-like, fruity and sweet.

As aprotic solvents for the extraction of the appropriate materials, the solvents advantageously used are those permissible in the food industry. Examples of such applicable aprotic solvents are alkanes having 5–10 carbon atoms, such as pentane and hexane, cycloalkanes having 6–10 carbon atoms, such as cyclohexane, and ethers having 2–6 carbon atoms, such as diethyl ether and methyl-tert.butyl ether. Also aprotic chlorinated solvents such as chloroform and dichloromethane can be used, as well as ketones such as methylethylketone and acetone. The solvents used are removed from the final product after the performance of the photochemical conversion. This applies in particular when the final product is used as flavour component.

The vegetable materials used in the extraction normally have a carotene content of less than 1% by weight. After extraction with an aprotic solvent, usually unsaturated solutions are obtained. These solutions can, if desired, be concentrated to saturated solutions. Further, saturated solutions can be prepared on the basis of commercially available carotene products.

The product obtained by the extraction of the vegetable material or, as the case may be, micro-organism, can, if desired, be purified by for instance chromatography over usual column materials, such as basic aluminium oxide and magnesium oxide with, inter alia, hexane as eluent.

For the ultraviolet irradiation, known sources of ultraviolet light can be used. Very suitable is a high-pressure mercury lamp which has optionally been enriched with halogenides. The wavelength range to be used is 200–700 nm and is advantageously 350–560 nm. The duration of irradiation depends mainly on the carotene concentration in the solution, since the irradiation is generally continued until the solution has been completely or substantially decolourized.

During the irradiating of the carotene-containing solution an oxygen-containing gas mixture such as air is passed through. As well as air, pure oxygen or an oxygen/air mixture can also be used. The temperature applied during the irradiation of the carotene-containing solution can vary over a broad range, whereby the lower temperature of the range depends on the solubility of the carotene product in the aprotic solvent used and the upper temperature of the range is in principle connected with the boiling temperature of the solvent concerned. Advantageously, the temperature is in the range of 10°–40° C. For simplicity's sake the irradiation is preferably carried out at ambient temperature or room temperature.

For use as fragrance material, the product obtained can be used as such as fragrance-imparting agent, as well as being used successfully in all kinds of perfume compositions.

By the expression "perfume composition" is meant here a mixture of fragrance materials and possible adjuvants, dissolved if so desired in a suitable solvent or mixed with a powdery substrate, that is used in order to impart a desired fragrance to the skin and/or a variety of products. Examples of such products are: soaps, detergents, air fresheners, room sprays, pomanders, candles, cosmetics such as creams, balms, toilet waters, pre- and aftershave lotions, talcum powders, hair care agents, body deodorants and anti-perspirants.

Fragrance materials and mixtures thereof which can be used in combination with the product according to the invention for the preparation of perfume compositions are for example: natural products such as essential oils, absolutes, resinoids, resins, concrêtes etc., but also synthetic fragrance materials such as hydrocarbons, alcohols, aldehydes, ketones, ethers, acids, esters acetals, ketals, nitriles etc., including saturated and unsaturated compounds, aliphatic, carbocyclic and heterocyclic compounds. Examples of fragrance materials which can be used in combination with the compounds according to the invention are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethyl-phenylcarbinyl acetate, p-tert.butylcyclohexyl acetate, isononyl acetate, vetiveryl acetate, vetiverol, α-hexylcinnamic aldehyde, 2-methyl-3-(p-tert.butylphenyl)propanal, 2-methyl-3-(p-isopropylphenyl)propanal, 3-(p-tert.butylphenyl)propanal, tricyclodecenyl acetate, tricyclodecenyl propionate, 4-(4-hydroxy-4-methylpentyl-3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentylcyclopentane, 2-n-heptyl cyclopentanone, 3-methyl-2-pentyl-2-cyclopentanone, n-decenal, n-dodecanal, dec-9-en-1-ol, phenoxyethyl isobutyrate, phenylacetaldehyde dimethylacetal, phenylacetaldehyde diethylacetal, geranyl nitrile, citronellyl nitrile, cedryl acetate, 3-isocamphyl cyclohexanol, cedrylmethyl ether, isolongifolanone, aubepine nitrile, aubepine, heliotropine, coumarin, eugenol, vanillin, diphenyl oxide, hydroxycitronellal, ionones, methylionones, iso-methylionones, irones, cis-3-hexenol and esters thereof, indane-musk fragrances, tetraline-musk fragrances, isochromane-musk fragrances, macrocyclic ketones, macrolactone-musk fragrances, ethylene brassylate, aromatic nitro-musk fragrances.

Adjuvants and solvents which can be used in perfume compositions containing a product according to the invention are for example: ethanol, isopropanol, diethylene glycol monoethyl ether, diethyl phthalate etc.

The amounts in which the product according to the invention can be used in perfume compositions or materials to be perfumed can vary within wide limits and depend inter alia on the nature of the material in which the fragrance material is used, on the nature and amounts of the other components in the perfume compositions and on the fragrance effect aimed at. Therefore it is only possible to indicate very global limits, with which, however, the expert is provided with sufficient information to be able to use the products of the invention on his own. In most cases an amount of merely 0.001% by weight in a perfume composition will be quite sufficient for obtaining a clearly perceptible fragrance effect. On the other hand for the preparation of special fragrance effects, it is possible to use an amount of 30% by weight or even more in a composition. In materials perfumed with the aid of perfume compositions these concentrations are proportionally lower, depending on the amount of composition used in the material.

Further, the products according to the invention can be added as such to foodstuffs and stimulants, or can first be mixed with carriers or solvents customary in the flavour industry. Preferably, however, they are incorporated in flavour compositions. By the expression "flavour composition" is meant in this connection a mixture of flavour materials of natural and/or synthetic origin, dissolved, if desired, in a suitable solvent or mixed with a powdery substrate in order to impart a desired taste to all kinds of foodstuffs and stimulants. By "foodstuffs and stimulants" are meant: solid or liquid products, intended for human consumption, also including tobacco products, pharmaceuticals and toothpaste.

Flavour materials of natural or synthetic origin, which can be combined in flavour compositions with the products according to the invention, are named for example in S. Arctander, Perfume and Flavor Chemicals (Montclair, N.J., 1969), in S. Arctander, Perfume and Flavor Materials of Natural Origin (Elisabeth, N.J., 1960), in T. E. Furia et al., CRC Fenaroli's Handbook of Flavor Ingredients, 2nd ed. (Cleveland, CRC Press Inc., 1975) and in H. B. Heath, Source Book of Flavors, (The AVI Publishing Company Inc., Westport, Conn., 1981).

The amounts in which the products according to the invention can be used in flavour compositions or products to be flavoured can vary within wide limits and depend inter alia on the nature of the product in which the compounds are used, on the nature and the amount of the other flavour components in the flavour compositions and on the flavour effect aimed at. Therefore it is only possible to indicate very global limits, with which, however, sufficient information is provided for the expert to be able to use the products according to the invention on his own. For instance, the products according to the invention can be included in an amount of 0.01–100 ppm in the foodstuffs or stimulants to be flavoured.

The following examples serve exclusively to illustrate the preparation and use of the products according to the invention. However, the invention is not limited thereto.

EXAMPLE I

A diluted solution of 1 g crystalline synthetic β-carotene in 100 ml cyclohexane, which was in a cylindrical vessel, was irradiated while being stirred at room temperature (20° C.) with a 150 Watt high-pressure mercury lamp having a wavelength range of 350-560 nm (manufactured by: Hereaus) while 6 ml air/minute was passed through, until the solution after approximately 50 hours was completely decolourized.

After the solvent had been distilled off, 0.95 g flavour material was obtained that had a fresh, fruity, saffron-like, sweet and yellow odour character and could be used in, inter alia, fruit flavours, tobacco flavours and also as a fragrance material.

When methyl-tert.butyl ether was used instead of cyclohexane a similar product was obtained.

EXAMPLE II

An amount of 250 g paprika powder was extracted twice, while being stirred, with 500 ml ether/cyclohexane (1:1). After the solvents had been distilled off, the residue was saponified in a mixture of 750 ml water/methanol (1:2) and 10 ml 50% KOH while being boiled for 1 hour. The mixture was extracted with cyclohexane and this extract was purified by chromatography over silica with cyclohexane as eluent. The product thus purified was irradiated as solution in cyclohexane while being stirred at room temperature (20° C.) with air being passed through in accordance with Example I, with a high-pressure mercury lamp until the solution had decolourized. After the organic solvent had been distilled off, a flavour material having a fruity, sweet and fresh character was obtained that could be used, for example, in fruit flavours.

EXAMPLE III

A mixture of 50 g green tea and 50 ml water was heated for 1 hour at 50° C. while being stirred. Subsequently, with stirring, a mixture of 150 ml methanol/hexane (2:1) was added to the resulting slurry and the stirring was continued for 1 hour at 50° C. After 50 ml 5% aqueous NaCl solution and 50 ml hexane had been added, the carotene pigments were isolated (according to standard procedures) by means of evaporating the hexane phase. Subsequently, the carotene-containing mixture obtained was dissolved in cyclohexane and, with the aid of the high-pressure mercury lamp used in Example I, irradiated for 24 hours at room temperature (20° C.). After the solvent had been distilled off, a flavour material having a hay-like, fatty, radiant and tobacco-like character was obtained that, inter alia, could be used to good effect on tobacco and also as a fragrance material.

EXAMPLE IV

| TEA FLAVOUR | |
|---|---|
| | parts by weight |
| Tea extract | 700 |
| Ethanol | 256 |
| Tincture of chirette | 12 |
| Bergamot oil | 5 |
| Foin abs. sol.* | 5 |
| Acetic acid sol.* | 5 |
| Maté abs. sol.* | 4 |
| Davana oil sol.* | 4 |
| Sauge sclaree sol.* | 4 |
| Mixture according to Example III** | 5 |
| Total | 1000 |

*as 1% solution in ethanol.
**as 5% solution in ehanol.

EXAMPLE V

| RASPBERRY FLAVOUR MIXTURE | |
|---|---|
| | parts by weight |
| Benzyl acetate | 500 |
| Amyl acetate | 250 |
| Benzyl alcohol | 182 |
| Geraniol | 5 |
| Citronellol | 4 |
| Ethyl valerianate | 2 |
| Isobutyl acetate | 2 |
| gamma-Undecalactone | 2 |
| Vanillin | 2 |
| Phenylethyl alcohol | 1 |
| Mixture according to Example I* | 50 |
| Total | 1000 |

*as 5% solution in ethanol.

EXAMPLE VI

| PERFUME FOR SHAMPOO | |
|---|---|
| | parts by weight |
| Bergamot oil reconstitué | 150 |
| α-Amylcinnamic aldehyde | 150 |
| Muguet base | 150 |
| Benzyl acetate | 70 |
| Traseolide | 50 |
| Lemon oil | 40 |
| Benzyl salicylate | 35 |
| Bulgarian attar of roses reconstitué | 30 |
| Undecanal* | 20 |
| Coumarin | 15 |
| Benzoin Siam resinoid | 15 |
| Isoeugenyl acetate | 15 |
| 11-Oxahexadecanolide | 10 |
| 2-Methylundecanal* | 10 |
| Dodecanal* | 10 |
| Costus oil reconstitué | 10 |
| Mousse de chêne absolue | 5 |
| Methyl eugenol | 5 |
| Iris oil | 5 |
| gamma-Undecalactone* | 5 |
| Mixture according to Example I** | 50 |
| Total | 800 |

*as 10% solution in dipropylene glycol.
**as 5% solution in ethanol.

EXAMPLE VII

| VIRGINIA FLAVOUR | |
|---|---|
| | parts by weight |
| Benzyl alcohol | 263 |
| gamma-Butyrolactone | 250 |
| Ethyl palmitate | 200 |
| Acetic acid | 60 |
| gamma-Valerolactone | 60 |
| Farnesol | 25 |
| Valeric acid | 20 |
| gamma-Heptalactone | 20 |
| Ethyl laurate | 20 |
| Ethyl decanoate | 10 |
| Malt extract (20% dry matter) | 10 |
| Coffee extract | 10 |
| Furfural | 10 |
| Guaiacol | 5 |
| Benzaldehyde | 4 |
| Acetophenone | 4 |
| Methylheptenone | 4 |
| Mixture according to Example III* | 25 |
| Total | 1000 |

*as 5% solution in ethanol.

EXAMPLE VIII

PAELLA FLAVOUR MIXTURE

|  | parts by weight |
|---|---|
| Salt: NaCl | 288 |
| Paprika powder | 300 |
| Garlic powder | 250 |
| Pepper | 100 |
| Capsicum | 10 |
| Bay leaf | 1 |
| Thyme | 1 |
| Mixture according to Example II* | 50 |
| Total | 1000 |

*as 5% solution in ethanol.

EXAMPLE IX

ROSE PERFUME

|  | parts by weight |
|---|---|
| Phenylethyl alcohol | 465 |
| Geraniol | 100 |
| Citronellol | 100 |
| Rose absolue** | 50 |
| Phenylethyl acetate | 40 |
| Trichloromethylphenylcarbinyl acetate | 30 |
| Geranium oil | 30 |
| Undecen-10-al* | 25 |
| Oil of cloves | 20 |
| Phenylacetaldehyde dimethylacetal | 20 |
| Hydroxycitronellal | 20 |
| Undec-10-en-1-ol* | 20 |
| Ylang-ylang oil | 10 |
| Benzyl acetate | 10 |
| Citronellyl acetate | 10 |
| Cinnamic alcohol | 10 |
| Nonanol-1* | 10 |
| Methylphenyl acetate | 5 |
| Isobutyl salicylate | 5 |
| Tincture of musk | 5 |
| Mixture according to Example III*** | 15 |
| Total | 1000 |

*as 10% solution in dipropylene glycol.
**as 10% solution in ethanol.
***as 5% solution in ethanol.

EXAMPLE X

TOMATO FLAVOUR MIXTURE

|  | parts by weight |
|---|---|
| 2-Ethylhexanol | 200 |
| Dimethyl sulphide* | 130 |
| Amyl valerianate | 130 |
| Cis-3-hexenol | 120 |
| 3-Methylbutanal | 100 |
| Amyl butyrate | 50 |
| Isobutanol | 50 |
| Butyl hexanoate | 50 |
| Hexanal | 50 |
| Methyl salicylate | 20 |
| Hexyl acetate | 15 |
| Amyl acetate | 15 |
| Benzaldehyde | 15 |
| Linalool oxide | 15 |
| Geranylacetone | 3 |
| Hexen-2-al | 3 |
| Cinnamic aldehyde | 2 |
| Citronellal | 2 |
| Methional | 2 |
| 2-Isobutylthiazole | 2 |
| 2-Acetylthiazole | 1 |
| Mixture according to Example II** | 25 |
| Total | 1000 |

*as 1% solution in ethanol.
**as 5% solution in ethanol.

EXAMPLE XI

PIPE TOBACCO FLAVOUR MIXTURE

|  | parts by weight |
|---|---|
| Propylene glycol | 536 |
| Apricot oleoresin | 350 |
| Vanillin | 80 |
| Ylang-ylang oil (10% alcohol) | 5 |
| Coriander oil | 2 |
| Mixture according to Example I* | 25 |
| Total | 1000 |

*as 5% solution in ethanol.

EXAMPLE XII

WHITE WINE FLAVOUR MIXTURE

|  | parts by weight |
|---|---|
| Coriander oil | 355 |
| Davana oil | 200 |
| Sauge sclaree oil | 200 |
| Methyl N-methylanthranilate | 100 |
| Geranium oil Bourbon | 100 |
| Sureau pays abs. | 40 |
| Mixture according to Example I* | 5 |
| Total | 1000 |

*as 5% solution in ethanol.

We claim:

1. A process for the preparation of a product which is useful as a flavor or fragrance material which comprises oxidizing a solution of carotene in an aprotic solvent with oxygen under the influence of ultraviolet light and subsequently substantially removing the aprotic solvent from the product.

2. Process according to claim 1, wherein the carotene is of synthetic origin.

3. Process according to claim 2, wherein a solution of synthetic crystalline β-carotene in an aprotic solvent is used as carotene-containing solution.

4. Process according to claim 1, wherein the carotene is obtained by extraction of carotene-containing vegetable material or micro-organisms, which are suitable for human consumption, with an aprotic solvent or solvent mixture.

5. Process according to claim 1 wherein at least one member selected from the group consisting of an alkane having 5-10 carbon atoms, a cycloalkane having 6-10 carbon atoms and an ether having 2-6 carbon atoms is used as aprotic solvent.

6. Process according to claim 5 wherein hexane, cyclohexane, diethyl ether or methyl-tert.butyl ether is used as aprotic solvent.

7. Process according to claim 1, wherein the irradiation with ultraviolet light is carried out in the range of 350-560 nm.

8. Process according to claim 1, wherein the irradiation with ultraviolet light is carried out at a temperature in the range of 10°-40° C.

9. Process according to claim 1, wherein air is used as source of oxygen.

10. Process according to claim 1, wherein the aprotic solvent is separated from the product by means of distillation.

11. Perfume or flavor composition comprising an effective amount of a fragrance or flavor material obtained by oxidizing a solution of carotene in an aprotic solvent with oxygen under the influence of ultraviolet light to form a product comprising a fragrance or flavor material and subsequently removing the aprotic solvent from the product.

* * * * *